United States Patent
Freeman et al.

(10) Patent No.: US 10,441,186 B2
(45) Date of Patent: Oct. 15, 2019

(54) ELECTRODE PADSET

(71) Applicant: Respiratory Motion, Inc., Lexington, MA (US)

(72) Inventors: Jenny E. Freeman, Weston, MA (US); Michael Lalli, Haverhill, MA (US); Malcom G. Bock, Medfield, MA (US); Elizabeth Klodd, Brookline, MA (US); Jordan Brayanov, Medford, MA (US)

(73) Assignee: Respiratory Motion, Inc., Watertown, MA (US)

( * ) Notice: Subject to any disclaimer, the term of this patent is extended or adjusted under 35 U.S.C. 154(b) by 761 days.

(21) Appl. No.: 14/021,939

(22) Filed: Sep. 9, 2013

(65) Prior Publication Data

US 2014/0073895 A1     Mar. 13, 2014

Related U.S. Application Data

(60) Provisional application No. 61/698,289, filed on Jul. 9, 2012, provisional application No. 61/698,257, filed
(Continued)

(51) Int. Cl.
*A61B 5/04*     (2006.01)
*A61B 5/0408*     (2006.01)
(Continued)

(52) U.S. Cl.
CPC ........ *A61B 5/04087* (2013.01); *A61B 5/0478* (2013.01); *A61B 5/04085* (2013.01);
(Continued)

(58) Field of Classification Search
CPC . A61B 5/0006; A61B 5/04087; A61B 5/0478; A61B 5/6833; A61B 5/0402;
(Continued)

(56) References Cited

U.S. PATENT DOCUMENTS

| | | |
|---|---|---|
| 593,441 A | 11/1897 | Stahlhut |
| 3,433,217 A | 3/1969 | Rieke |

(Continued)

FOREIGN PATENT DOCUMENTS

| | | |
|---|---|---|
| CN | 1034665 | 8/1989 |
| CN | 101496767 | 8/2010 |

(Continued)

OTHER PUBLICATIONS

PCT Search Report for PCT/US2013/058797, dated Feb. 25, 2014.
(Continued)

*Primary Examiner* — Joseph A Stoklosa
*Assistant Examiner* — Brian M Antiskay
(74) *Attorney, Agent, or Firm* — Remenick PLLC

(57) ABSTRACT

An electrode padset and a method of using the electrode padset are disclosed herein. The electrode padset is a single unit, consisting of multiple patient-contacting conductive pads arranged on a single piece of material. The padset is comprised of a plurality of conductive pads, at least one conductive pad adapted to emit an electrical signal and at least one other conductive pad adapted to receive an electrical signal, and an electrically conductive material coupling the conductive pads.

33 Claims, 18 Drawing Sheets

Related U.S. Application Data on Sep. 7, 2012, provisional application No. 61/808,509, filed on Apr. 4, 2013.

(51) Int. Cl.
*A61B 5/00* (2006.01)
*A61B 5/0478* (2006.01)
*A61B 5/0492* (2006.01)
*A61B 5/0428* (2006.01)
*H02G 11/02* (2006.01)

(52) U.S. Cl.
CPC ........ *A61B 5/0492* (2013.01); *A61B 5/04286* (2013.01); *A61B 5/6823* (2013.01); *A61B 5/6833* (2013.01); *A61B 5/0006* (2013.01); *A61B 2562/0285* (2013.01); *A61B 2562/227* (2013.01); *H02G 11/02* (2013.01)

(58) Field of Classification Search
CPC .......... A61B 5/0205; A61B 2560/0412; A61B 5/6804; A61B 5/6831; A61B 5/6823; A61N 1/0492; A61N 1/0476; A61N 1/0484; A61N 1/0496
USPC ................ 600/372, 382–384, 386, 388–393, 600/508–509
See application file for complete search history.

(56) References Cited

U.S. PATENT DOCUMENTS

| | | | |
|---|---|---|---|
| 3,690,143 A | 9/1972 | Day | |
| 3,742,936 A | 7/1973 | Blanie | |
| 4,036,217 A | 7/1977 | Ito | |
| 5,058,583 A | 10/1991 | Geddes et al. | |
| 5,341,806 A * | 8/1994 | Gadsby | A61B 5/04085 600/391 |
| 5,813,979 A * | 9/1998 | Wolfer | A61B 5/04286 600/373 |
| 6,168,568 B1 | 1/2001 | Gavriely | |
| 6,173,198 B1 | 1/2001 | Schulze et al. | |
| 6,286,806 B1 | 9/2001 | Cocoran | |
| 6,366,803 B1 | 4/2002 | Fee | |
| 6,402,697 B1 | 6/2002 | Calkins et al. | |
| 6,809,462 B2 | 10/2004 | Pelrine et al. | |
| 6,976,963 B2 | 12/2005 | Clift | |
| 7,196,317 B1 | 3/2007 | Meissner et al. | |
| 7,245,974 B2 * | 7/2007 | Dupelle | A61N 1/0492 607/142 |
| 7,361,146 B1 | 4/2008 | Bharmi et al. | |
| 7,530,956 B2 | 5/2009 | Lewicke et al. | |
| 7,844,316 B1 * | 11/2010 | Botero | A61B 5/04286 439/909 |
| 8,019,402 B1 * | 9/2011 | Kryzpow | A61B 5/04085 600/386 |
| 8,096,962 B2 | 1/2012 | Palazzolo | |
| 8,571,627 B2 * | 10/2013 | Tremblay | A61B 5/04085 600/382 |
| 8,781,551 B2 | 7/2014 | Chetham | |
| 2002/0032383 A1 | 3/2002 | Weil et al. | |
| 2004/0071337 A1 | 4/2004 | Jeung et al. | |
| 2004/0123667 A1 | 7/2004 | McGrath | |
| 2004/0236202 A1 * | 11/2004 | Burton | A61B 5/0536 600/384 |
| 2005/0033198 A1 | 2/2005 | Kehyayan et al. | |
| 2005/0107719 A1 | 5/2005 | Arad | |
| 2005/0113702 A1 | 5/2005 | Salla et al. | |
| 2006/0058600 A1 | 3/2006 | Eichler | |
| 2006/0070623 A1 | 4/2006 | Wilkinson | |
| 2006/0241506 A1 | 10/2006 | Melker et al. | |
| 2006/0241513 A1 | 10/2006 | Hatlestad | |
| 2007/0010764 A1 | 1/2007 | Palazzolo et al. | |
| 2007/0027388 A1 * | 2/2007 | Chou | A61B 5/0002 600/393 |
| 2007/0276300 A1 | 11/2007 | Olson et al. | |
| 2008/0312565 A1 | 12/2008 | Celik-Butler et al. | |
| 2009/0062672 A1 | 3/2009 | Sly et al. | |
| 2009/0149748 A1 | 6/2009 | Lenhardt et al. | |
| 2009/0264789 A1 | 10/2009 | Molnar et al. | |
| 2009/0264792 A1 | 10/2009 | Mazar | |
| 2009/0326253 A1 | 12/2009 | Watson et al. | |
| 2009/0326353 A1 | 12/2009 | Watson et al. | |
| 2010/0152600 A1 | 6/2010 | Droitcour | |
| 2010/0228166 A1 | 9/2010 | Centen | |
| 2010/0241181 A1 | 9/2010 | Savage et al. | |
| 2011/0077497 A1 | 3/2011 | Oster et al. | |
| 2011/0245712 A1 | 10/2011 | Patterson et al. | |
| 2011/0288605 A1 * | 11/2011 | Kaib | A61B 5/0006 607/5 |
| 2011/0306850 A1 | 12/2011 | Hatlestad et al. | |
| 2012/0041279 A1 | 2/2012 | Freeman et al. | |
| 2012/0165883 A1 | 6/2012 | Kalgren et al. | |
| 2013/0187941 A1 | 7/2013 | Noon | |
| 2013/0296823 A1 | 11/2013 | Melker et al. | |
| 2014/0073895 A1 | 3/2014 | Brayanov | |
| 2015/0231387 A1 * | 8/2015 | Harding | A61B 5/686 600/393 |
| 2016/0113535 A1 * | 4/2016 | Marek | A61B 5/0404 600/384 |

FOREIGN PATENT DOCUMENTS

| | | |
|---|---|---|
| CN | 102065751 | 6/2015 |
| EP | 1302217 | 4/2003 |
| EP | 2008581 | 12/2008 |
| EP | 2018825 | 1/2009 |
| JP | 2000-70370 | 3/2000 |
| JP | 2007-203041 | 8/2007 |
| JP | 2009-240752 | 10/2009 |
| WO | WO00/33733 | 6/2000 |
| WO | WO2007/064682 | 6/2007 |
| WO | WO2007/147505 | 12/2007 |
| WO | WO2008/130549 | 10/2008 |
| WO | WO2009/035965 | 3/2009 |
| WO | WO2009/036312 | 3/2009 |
| WO | WO2010/059049 | 5/2010 |

OTHER PUBLICATIONS

EP Office Action for PCT/US2011/47812, dated Mar. 11, 2015.
Zulkarneev R Kh. Et al., A Hardware-Software System for Volumetric Calibration of Impedance Pneumograms, Biomedical Engineering, vol. 35, No. 1, 2001, pp. 48-51.
U.S. Appl. No. 13/210,360, filed Feb. 16, 2012, Freeman.
U.S. Appl. No. 13/554,346, filed Jan. 24, 2013, Freeman.
Pajic, et al, Model-driven safety analysis of closed-loop medical systems, IEEE Trans Industr Inform. vol. 10, pp. 1-35, p. 4, para. 1-2, Oct. 28, 2013.
PCT Search Report for PCT/US15/59032, dated Feb. 4, 2016.
CL Office Action for Application No. 201500579, dated Jun. 3, 2015.
CN Office Action for Application No. 201380057998.2, dated Jun. 28, 2016.
EPO Search Report for PCT/US2013/058797, dated Jul. 16, 2016.
U.S. Appl. No. 13/554,346, filed Jul. 20, 2012, Freeman.
U.S. Appl. No. 12/667,216, filed Dec. 23, 2010, Freeman.
U.S. Appl. No. 61/449,811, filed Mar. 7, 2011, Panasyuk.
U.S. Appl. No. 61/509,952, filed Jul. 20, 2011, Freeman.
U.S. Appl. No. 61/480,105, filed Apr. 28, 2011, Robinson.
PCT Search Report for PCT/US2011/47812, dated Jan. 10, 2012.
PCT Patentability Report for PCT/US2011/47812, dated Jan. 10, 2012.
PCT Patentability Report for PCT/US2008/76224, dated Mar. 16, 2010.
EP Search Report for PCT/US2011/047812, dated Feb. 19, 2014.
PCT Search Report for PCT/US2012/47604, dated Oct. 12, 2012.
PCT Patentability Report for PCT/US2012/47604, dated Oct. 12, 2012.
PCT Search Report dated Nov. 10, 2008.

(56) References Cited

OTHER PUBLICATIONS

PCT Patentability Report dated Nov. 10, 2008.
U.S. Appl. No. 12/677,216, Freeman.
U.S. Appl. No. 13/210,360, Freeman.
U.S. Appl. No. 13/554,346, Freeman.
EPO Search Report for PCT/US2011/047812, dated Feb. 19, 2014.
CN Office Action for Application No. 201380057998.2, dated Aug. 24, 2017.
EP Office Action for PCT/US2010/047604, dated Mar. 5, 2015.
Japenese Office Action for PCT/US2011/047812, dated Mar. 2, 2015.
Korean Office Action for App. No. 10-2015-7008867, dated Oct. 10, 2018.

* cited by examiner

5-WIRE OPENING

3-WIRE OPENING

BEGINNING INSERTION

COMPLETE CONNECTION

ELECTRODE PADSET

REFERENCE TO RELATED APPLICATIONS

The present application claims priority to Provisional U.S. Application Nos. 61/698,289 and 61/698,257, both filed Sep. 7, 2012, and 61/808,509, filed Apr. 4, 2013, all entitled "Electrode Padset," and all of which are incorporated herein in their entirety.

BACKGROUND

1. Field of the Invention

The invention is directed to electrode padsets. Specifically, the invention is directed to patient-contacting conductive pads arranged on a single piece of material.

2. Background of the Invention

Medical electrodes transfer the energy of ionic currents in the body into electrical currents that can be amplified, studied, and used to help make diagnoses. Medical electrodes permit surface quantification of internal ionic currents, yielding an ordinarily non-invasive test for a variety of nervous, muscular, ocular, cardiac, and other disorders that might otherwise have required surgical means to verify their presence. For instance, muscular exams using electrodes may produce evidence of diminished muscle strength and can discriminate between primary muscle disorders and neurologically-based disorders, in addition to detecting if a muscle is truly weak or seems so due to other reasons. The electrodes are typically easy to use, fairly cheap, disposable (or easily sterilized), and often unique in the tasks they help to perform. The essential role of the electrode is to provide ideal electrical contact between the patient and the apparatus used to measure or record activity.

Medical electrodes are generally comprised of a lead or wire (for conduction of electrical current), a metal electrode, and electrode-conducting paste or gel for surface electrodes. There is also often a metal (for good electrical contact) snap for the lead to snap into place so that the electrode can be disposable while the lead can be reused. Existing electrode leads are usually designed to be a maximum in length to accommodate all size patients. However, when used with smaller patients, the extra length results in excess wires around the patient. The excess wires can be a source of discomfort and are a safety hazard because the wires can become caught when the patient moves in and out of bed or needs to have other procedures done in the hospital. Due to the length of existing leads, it is often difficult to keep the wires from tangling and to maintain appropriate application of the electrodes while minimizing the length of the leads.

SUMMARY OF THE INVENTION

The present invention overcomes the problems and disadvantages associated with current strategies and designs and provides new tools and methods of measuring physical parameters of a patient.

One embodiment of the invention is directed to an electrode padset. The padset comprises a plurality of conductive pads, at least one conductive pad adapted to emit an electrical signal and at least one other conductive pad adapted to receive an electrical signal and an electrically conductive material coupling the conductive pads to each other. The plurality of conductive pads are adapted to be placed on a patient in a specified configuration.

In a preferred embodiment, at least a portion of the electrically conductive material is adjustable to accommodate different size patients. The padset preferably further comprises at least one pouch, wherein each pouch maintains excess electrically conductive material not necessary to accommodate a patient. Preferably, at least one pouch is positioned above a conductive pad. In a preferred embodiment, the padset preferably further comprises at least one anti-creasing device coupled to each pouch preventing the electrically conductive material from creasing at fold points. Preferably, the padset further comprises a fixating device preventing the electrically conductive material from exiting each pouch unintentionally. Preferably, each pouch is open at both ends.

Preferably, the electrically conductive material is adapted to fold a plurality of times within each pouch. In a preferred embodiment, the electrode padset is a single unit. Preferably, the padset further comprises at least one of artwork, symbols, and indications to aid in the correct placement of the padset on a patient.

In a preferred embodiment, the electrode padset is adapted to acquire at least one of electrical bioimpedance (thoracic, cardiac or otherwise), electrocardiography (ECG), electroencephalography (EEG), and electromyography (EMG) signals. Preferably, the electrically conductive material is a vapor transmission material or a set of wires adjustable in length. Preferably, the padset is adapted to acquire at least one channel of tetrapolar transthoracic bioimpedance signals. Preferably, there are at least two bioimpedance channels and the bioimpedance channels are oriented at an angle between 0 and 90 degrees to each other. In a preferred embodiment, the padset is adapted to acquire a bilateral transthoracic bioimpedance signal.

Preferably, the specified configuration is anatomically relevant. Preferably, at least one conductive pad is coupled to a patient's mid-clavicular line, at least one conductive pad is coupled to the patient's mid-axillary line, and at least one conductive pad is coupled to the patient's xiphoid process.

The padset preferably further comprises a memory chip. Preferably, the memory chip stores at least one of calibration data, production data, patient data, expiration date data, and padset data. Preferably, the memory chip is capable of wireless communication. Preferably, the memory chip is passive and is couplable to an internal or external power supply.

Another embodiment of the invention is directed to a method of obtaining a bioimpedance signal. The method includes the steps of affixing the electrode padset as described herein to a patient, sending an electric signal from at least one conductive pad into the patient, receiving the electric signal from at least one conductive pad from the patient, and analyzing the received signal.

Another embodiment of the invention is directed to an electrode padset. The padset comprises a plurality of conductive pads and an electrically conductive material coupling the conductive pads at a distance from each other, wherein the electrically conductive material is adjustable to alter the distance between the conductive pads. Preferably, the conductive pads are adapted to receive electrical signals.

Another embodiment of the invention is directed to a connector adapted to couple an electrode padset to an electrical cable. The connector is comprised of a male connector coupled to the electrode padset and a female connector coupled to the electrical cable. The male connector comprised of a protrusion adapted to engage the female connector, a pair of flexible wings adapted to allow the protrusion to engage into and release from the female connector upon depression of the flexible wings by a force, wherein the flexible wings maintain a locked position when not depressed, and an orientation key. Upon engagement of the male connector into the female connector, an electrical circuit is formed.

Preferably, the electrode padset is disposable and the electrical cable is reusable. In a preferred embodiment, each edge of the male connector is rounded. Preferably, the protrusion is a triangular ramp and the female connector is comprised of a recess adapted to engage the triangular ramp. Preferably, the connector separates traces and contacts during engagement of the connector.

Another embodiment of the invention is directed to an electrode padset. The padset comprises a plurality of conductive pads, at least one conductive pad adapted to receive an electrical signal and an electrically conductive material coupling the conductive pads. The plurality of conductive pads are arranged in a specified configuration.

Preferably, at least a portion of the electrically conductive material is adjustable to accommodate different size patients. The padset preferably further comprises at least one pouch, wherein each pouch maintains excess electrically conductive material not necessary to accommodate a patient. Preferably, at least one pouch is positioned above a conductive pad. The padset preferably further comprises at least one anti-creasing device coupled to each pouch preventing the electrically conductive material from creasing at fold points. Preferably, the padset further comprises a fixating device preventing the electrically conductive material from exiting each pouch unintentionally.

In a preferred embodiment, each pouch is open at both ends. Preferably, the electrically conductive material is adapted to fold a plurality of times within each pouch. In a preferred embodiment, the electrode padset is a single unit. The padset preferably further comprises at least one of artwork, symbols, and indications to aid in the correct placement of the padset on a patient.

Preferably, the electrode padset is adapted to acquire at least one of electrical bioimpedance (thoracic, cardiac or otherwise), electrocardiography (ECG), electroencephalography (EEG), and electromyography (EMG) signals. In a preferred embodiment, the electrically conductive material is a vapor transmission material or is a set of wires adjustable in length. Preferably, the padset is adapted to acquire at least one channel of tetrapolar transthoracic bioimpedance signals. Preferably, there are at least two bioimpedance channels and the bioimpedance channels are oriented at an angle between 0 and 90 degrees to each other. The padset is preferably adapted to acquire a bilateral transthoracic bioimpedance signal. Preferably, the specified configuration specified configuration corresponds anatomically to a patient.

Preferably, the electrode padset is made from a single piece of material and has the electrodes laid out in a fixed configuration for ease and consistency of placement. Consistency of the placement of the electrodes is desirable to get accurate signals from the electrode array.

Preferably, the electrical electrode padset is connected to the trunk cable with a connector, which provides a convenient, slim, and snap fit connection.

Preferably, the padset is adapted to provide a disconnect force which is above a certain level, and provides an easily releasable connection when squeezed thereby releasing the snap connection.

Preferably the connector is compact and provides insulation between the conductive elements to prevent arcing during defibrillation in a size much smaller than conventional connectors.

Preferably, the padset is coupled to a passive memory chip which can store and transmit patient/padset specific information for later use.

Preferably, the padset is coupled to a power source, memory, and a wireless communication device, which can store and transmit patient/padset specific information for later use.

Other embodiments and advantages of the invention are set forth in part in the description, which follows, and in part, may be obvious from this description, or may be learned from the practice of the invention.

DESCRIPTION OF THE DRAWING

The invention is described in greater detail by way of example only and with reference to the attached drawing, in which.

DESCRIPTION OF THE INVENTION

Figure 1:
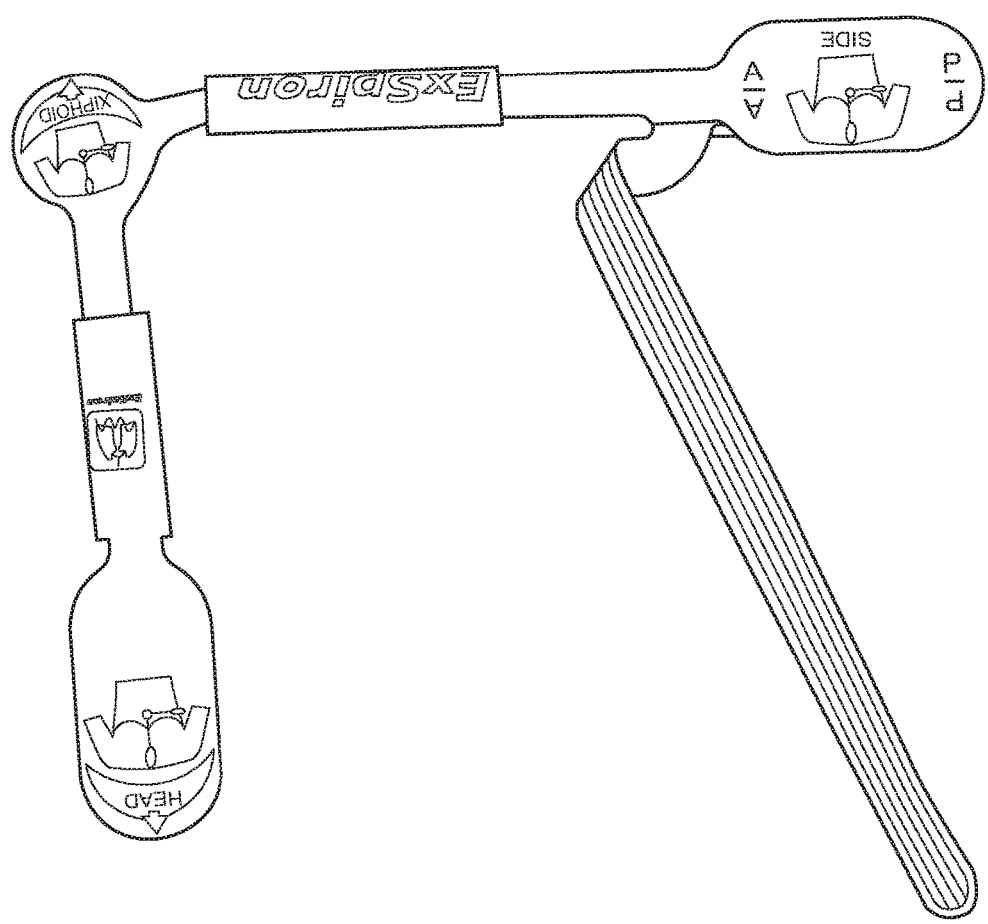
FIG. 1 is a photograph of an embodiment of an electrode of the invention.
Figure 2A:
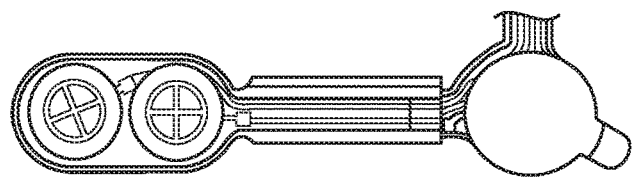
FIGS. 2a-h depict embodiments of various lengths of the electrode padset.
Figure 2B:
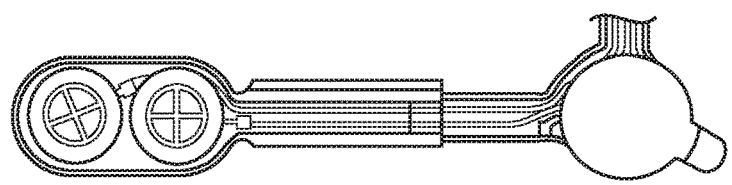
Figure 2C:
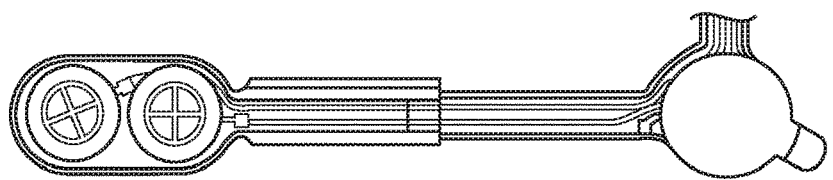
Figure 2D:
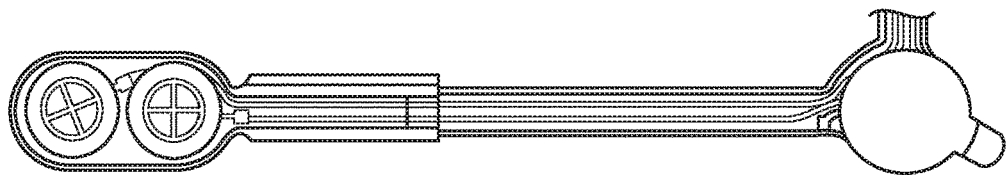
Figure 2E:
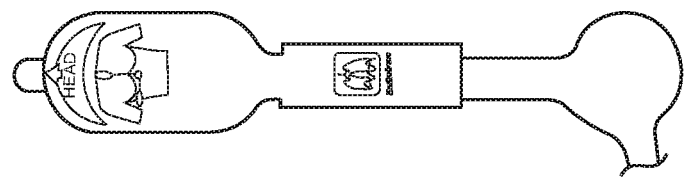
Figure 2F:
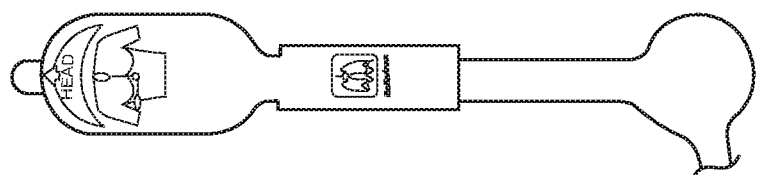
Figure 2G:
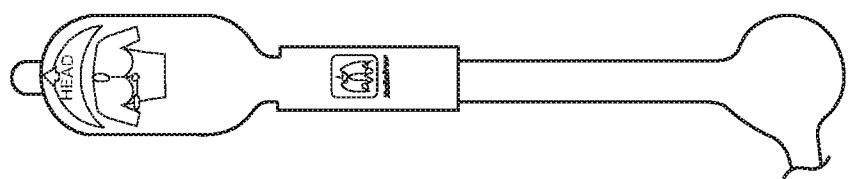
Figure 2H:
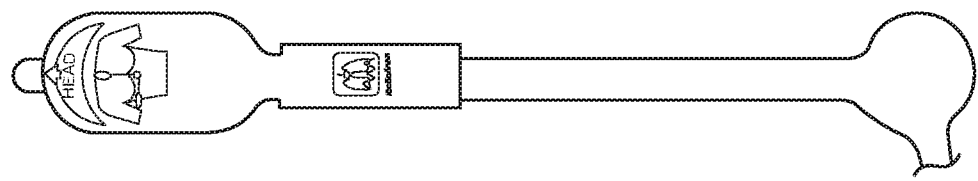

As embodied and broadly described herein, the disclosures herein provide detailed embodiments of the invention. However, the disclosed embodiments are merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention.

Medical electrodes currently utilize bulky and dedicated connectors for every lead that comes from the electrode set. It is desirable to have a connector that handles multiple leads and provides a slim and easy interconnect in making an electrical connection between a trunk cable to the monitor. It is also desirable to have a slim low profile connector in and around the patient that does not impose any hard edges against the patient. It is also desirable to have a connection system that provides a positive snap connection. It is also desirable to have a connector that requires a user to squeeze the connector to allow the connector to be positively disconnected. It is also desirable to have the connector able to be disconnected when the disconnect force exceed a certain level, even when the connector is not squeezed by the user. In circumstances when a cable gets tripped over or the monitoring equipment gets moved, it is desirable to have the connection disconnect when pulled above a certain force. This disconnect force would serve to eliminate the pull on the patient and the risk of knocking the monitoring equipment over inadvertently.

In a busy hospital environment, it is possible for a healthcare worker to select and use either an expired or inappropriate padset (e.g. a set of electrodes) on a patient. To address these issues, historically, hospital equipment and supplies have been carefully labeled and/or color-coded. Whereas these measures minimize the chance of a human error, they do not completely eliminate the problem. A solution is to recognize if and when a padset is inappropriately used, whether it is past its expiration date, or whether it has become faulty and communicate the problem to the end-user (healthcare provider).

When equipment relies on patient-specific calibration for optimal performance and when obtaining such calibration takes time, a challenge in using electrodes specific to custom monitoring parameters is, often, a patient has to be moved between different hospital departments (e.g. OR, ICU, PACU, or MRI) and it is not always feasible to move the monitoring equipment which holds the calibration data with the patient. A solution is to integrate the calibration information into the padset, which preferably remains attached to the patient, such that when the patient arrives in a new unit (e.g. PACU) the calibrations are transferred immediately into the bed-side monitor.

Current electrodes such as EKG can be difficult to apply and can be cumbersome when placed on the patient. Multi sensor electrodes can be difficult to apply in the correct anatomical landmarks and nurses seldom have the time and patience to apply the electrodes in a uniform and consistent fashion. It is beneficial to have an electrode which can be applied to the body, is adaptable to the size of the patient, and provides for proper placement by self alignment and graphical instructions when placed on the body.

FIG. 1 depicts an embodiment of an electrode padset. The electrode padset preferably is a single unit, consisting of multiple patient-contacting conductive pads arranged on a single piece of material. In another embodiment, multiple pieces of material joined are together into a single unit. The padset is adapted to be placed on a patient in a certain configuration to acquire bioelectrical signals including but not limited to electrical bioimpedance (thoracic, cardiac or otherwise), electrocardiography (ECG), electroencephalography (EEG) and electromyography (EMG). The capability of the padset in being preconfigured in the specific electrodes location and orientation can be seen in if FIG. 1. FIG. 1 is an example of an orthogonal arrangement used for the electrode sensor array. Preferably, the padset arranges the electrodes on the patient in an anatomically relevant configuration. For example, at least one conductive pad can be coupled to a patient's mid-clavicular line, at least one conductive pad can be coupled to the patient's mid-axillary line, and at least one conductive pad can be coupled to the patient's xiphoid process. The padset can also be affixed to the patient in different configurations. In the preferred embodiment, the padset is able to attach to one or more patient trunk cables.

Preferably, the padset includes artwork, symbols, or other indications to aid in the correct placement of the padset on the body. The padset is preferably made of plastic, fiber, nylon, or other medical grade materials that can be sanitized and sterilized.

The padset preferably includes at least one strip of material between the electrode pads which adjusts in length to fit patients of different sizes and body types. Preferably, the material is a vapor transmission material that allows the patient's skin to breathe and heal. For example, the material can be a cloth-like printed circuit (similar to a bandage), which is flexible and contours to the body. Preferably, the edges of the material between the electrode pads is formed (e.g. via laser cutting) to minimize sharp edges. Preferably, the edges of the material do not extend beyond the adhesive material used to affix the padset to the patient.

Figure 7:
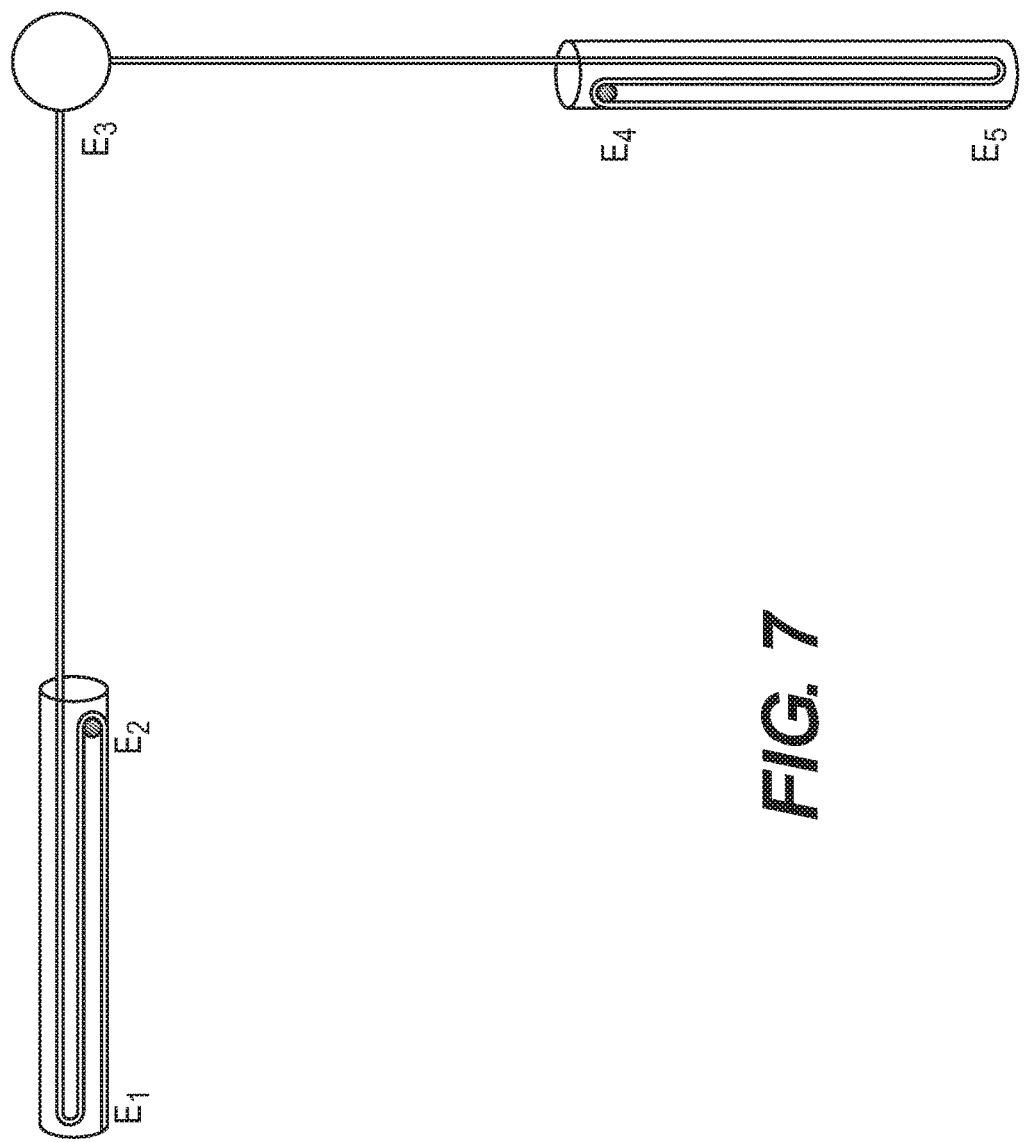
FIG. 7 depicts an embodiment of a padset with pouches positioned above the electrodes.
Figure 8:
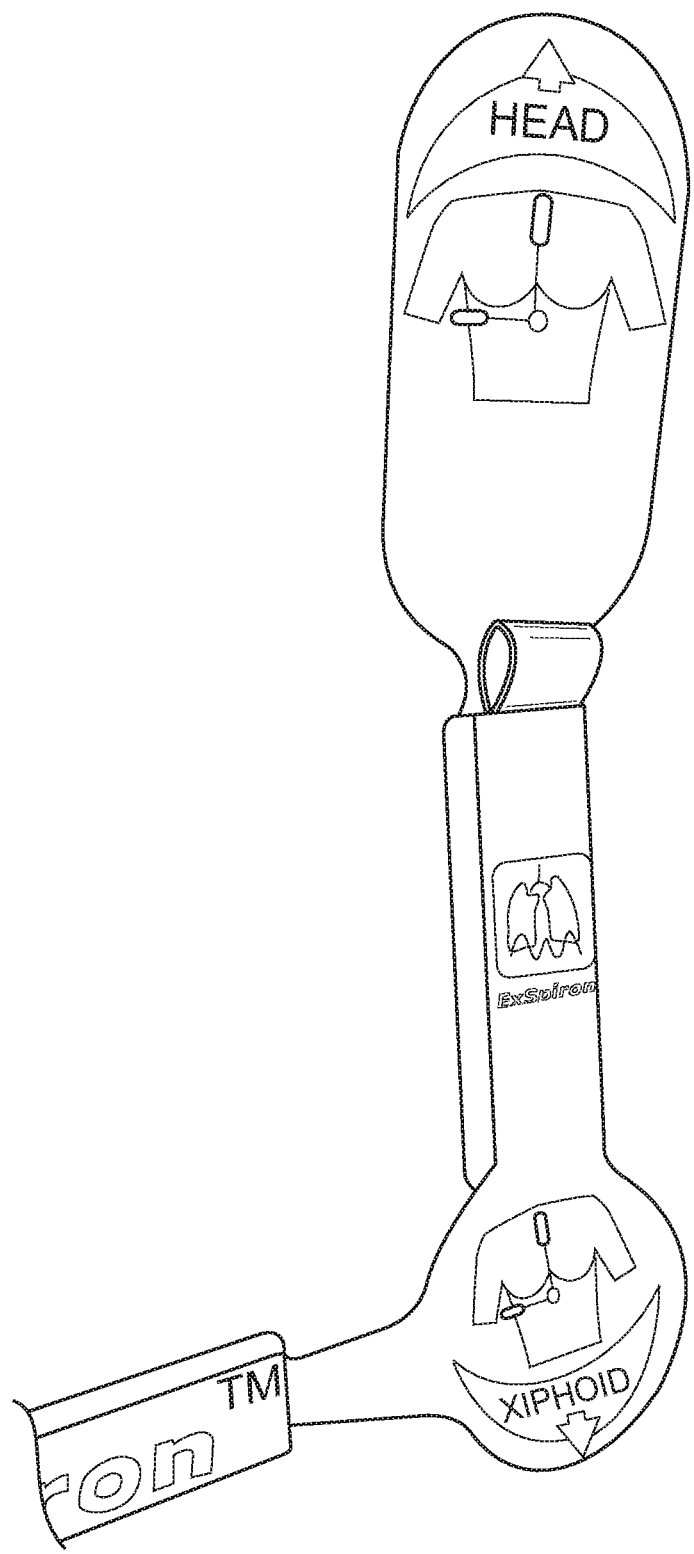
FIG. 8 depicts an embodiment of a padset with open-ended pouches.

In one embodiment, the padset is adjustable to fit different body parts. In another embodiment, the material between pads exerts a tension as it extends, but applies no tension once the user stops stretching the material. For example, the material can be elastic bands, lycra, or other stretchable materials. In another embodiment, the material between pads exerts a tension, thus holding the material close to the body. Unlike single wire cable which is flexible, low profile, and generally uses up very little space, printed film electrodes have minimal multi-directional flexibility and are therefore limited in the ability to accommodate excess length material in and around the patient. In another embodiment, the material between pads is sized to accommodate large body parts or large patients and there are provisions on the padset (e.g. pouches) to hold and contain the extra material kept the extra material out of the way. The pouch design provides for a low profile storage of excess length material, it also automatically manages the delivery and the geometry of this material so that the material interacts with the patient in a user friendly way. Preferably, the pouch is positioned above an electrode to simplify the arrangement of the padset (see FIG. 7). Additionally, as shown in FIG. 8, the pouch can be open at both ends. Having the pouch open at both ends, allows the circuit to be stored in a non-elongated state with a gentle radius at the fold points of the material at either end of the pouch. If the fold points were maintained within the pouch, it may be possible that the material would crease at the fold points, thereby damaging the circuit.

Figure 3:
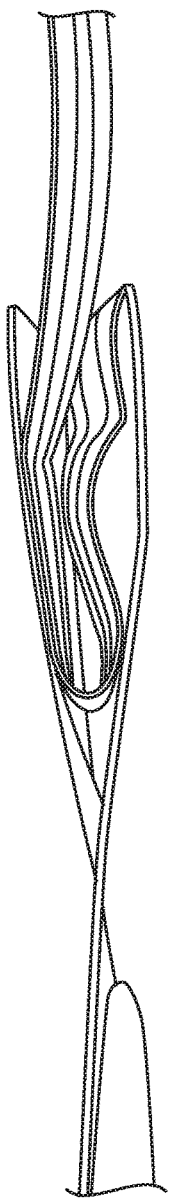
FIG. 3 depicts an embodiment of a printed film folded twice within a pouch.
Figure 4:
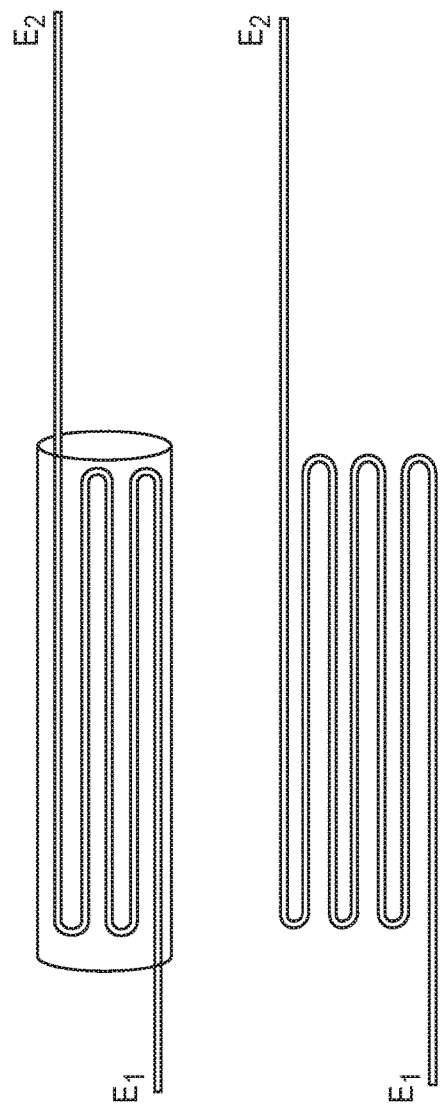
FIG. 4 depicts embodiments of a printed film folded multiple times within a pouch.

FIGS. 2a-h depict an embodiment of the padset having a pouch to hold excess printed film. As can be seen in the figures, the printed film can be extracted from the pouch to increase the distance between the electrodes. FIG. 3 depicts a cut away view of the printed film being extracted from the pouch. Preferably, the printed film is folded several times within the pouch. For example, as shown in FIG. 3, the printed film is folded twice. However, the printed film can be folded 4, 6, or 8 times causing multiple layers of the printed film (see FIG. 4). Preferably, the printed film can be removed from the pouch to lengthen the padset and reinserted into the pouch to shorten the padset.

Figure 5:
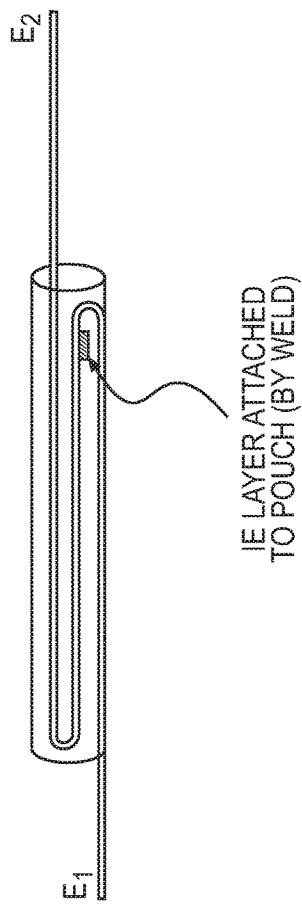
FIG. 5 depicts an embodiment of a printed film welded to a pouch.
Figure 6:
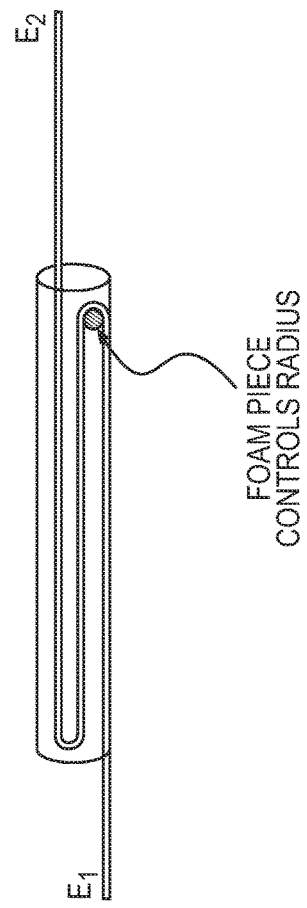
FIG. 6 depicts an embodiment of a printed film with a folding guide device.

When extending the padset, two problems can occur. First the friction between the layers can cause instances where multiple layers of printed film are withdrawn from the pouch at the same time, instead of one layer at a time. To prevent such multiple layer withdrawal, the intermediary layer can be affixed directly to pouch at a position near the pouch exit and hold the intermediary layer directionally so it will not exit the pouch with another layer. FIG. 5, for example, depicts a pouch with the intermediary layer welded to the pouch, which also prevents a user from pulling the printed film out of the pouch completely. Secondly, folding the printed film can damage the circuit and leave it inoperable. To solve this problem the circuit's fold can be controlled at the exit of pouch by the use of a small piece of foam or other guiding device, which serves to maintain a radius to protect the printed film at folding points. The foam, as shown in FIG. 6, allows for folding the printed film back on itself without damaging the circuit.

Figure 9A:
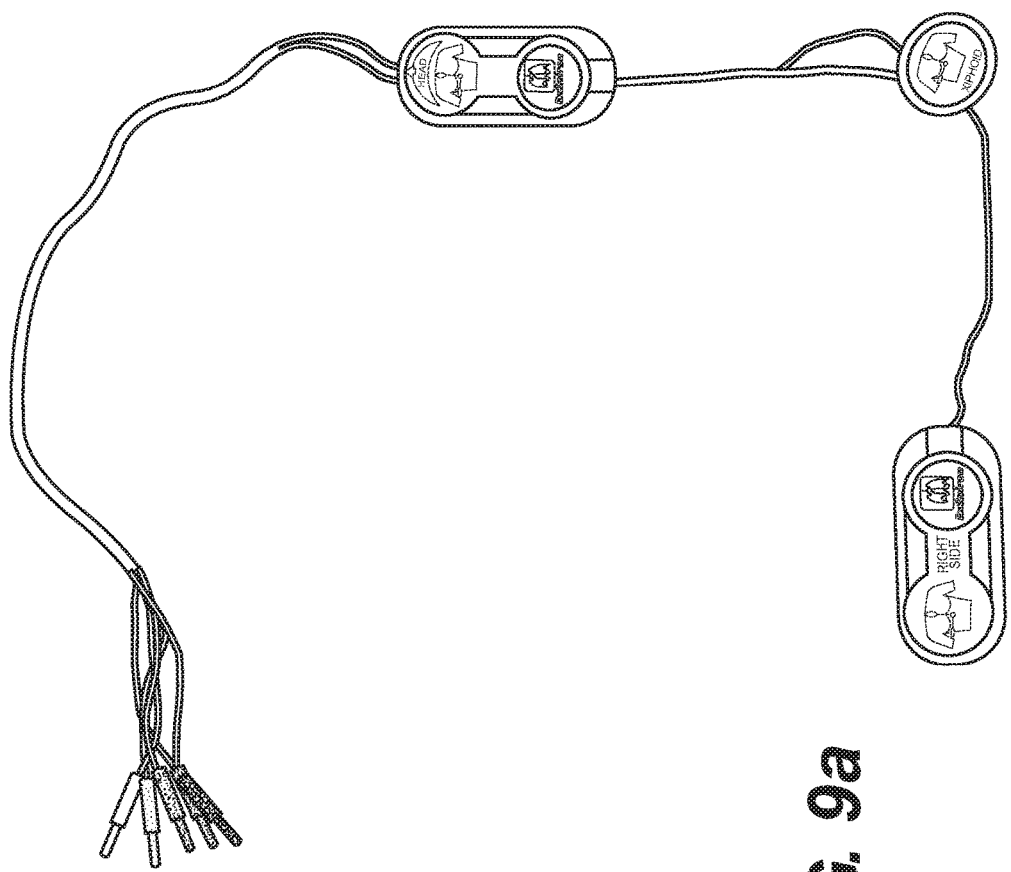
FIGS. 9a-b depict an embodiment of a padset with wire connectors.
Figure 9B:
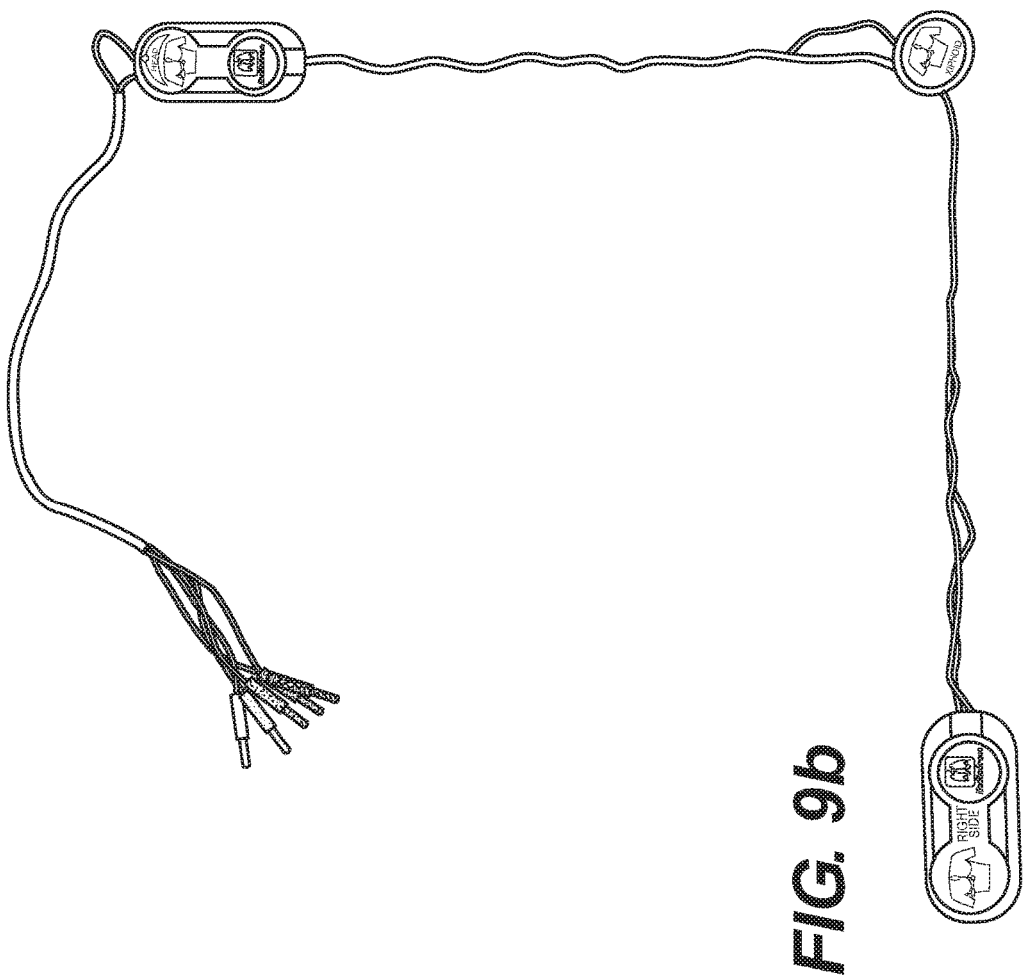
Figure 11:
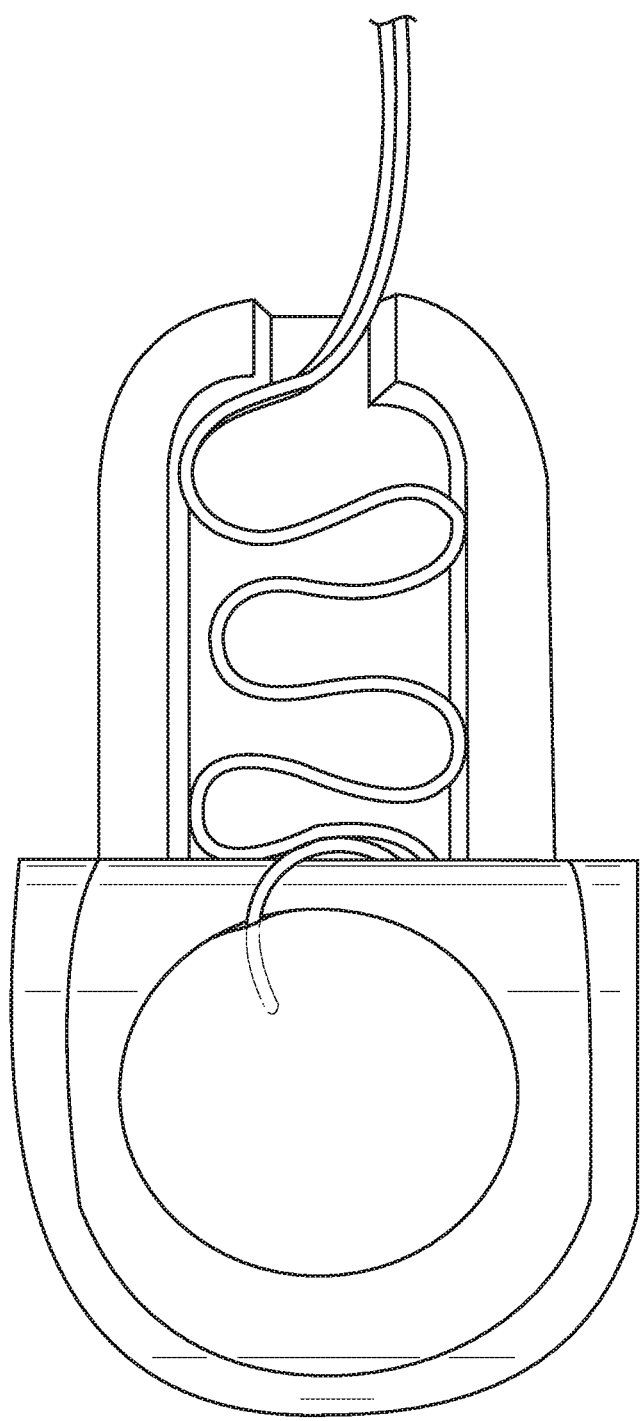
FIG. 11 depicts an embodiment of a wire in a pouch.

FIGS. 9a-b depict another embodiment of the padset. In the embodiment of FIGS. 9a-b, a wire or set of wires connects the electrodes. Preferably, a pouch or wire storage device is positioned above at least one electrode to maintain excess wire (as shown in FIG. 11). For example in FIG. 9a, the electrodes are positioned closer together with less wire between the electrodes. Thus, the excess wire is stored in pouches positioned above the electrodes. While, in FIG. 9b, the electrodes are positioned further apart with more wire between the electrodes. The flexible, closed-cell, molded foam preferably covers the top of the double electrodes to create the pouch, and has the ability to conform to contours of the body. The double electrode at the end of the wire preferably fits around the rib cage of the patient, and is able to conform to and stick to the patient as well as house the folded wiring.

Figure 10A:
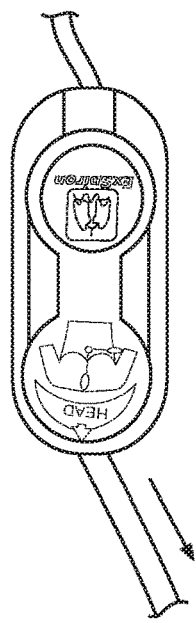
FIGS. 10a-c depict an embodiment of a pouch with directional openings.
Figure 10C:
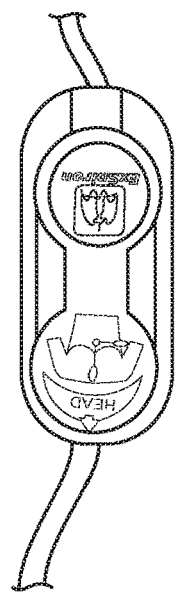
Figure 10B:
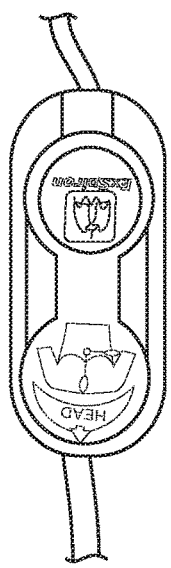
Figure 12:
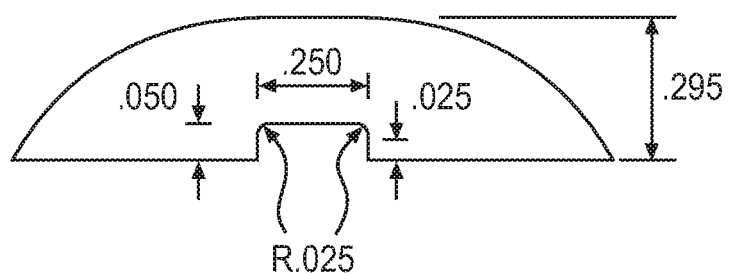
FIG. 12 depicts an embodiment of a wire opening sized to match wire size.

Additionally as depicted by the arrows in FIGS. 10a-c, using a wire to connect electrodes allows for the wire to exit the top of the "Head" electrode with the ability to point in the right, center, or left. This is achieved, for example, by incorporating notches in the exit hole so that the nurse or care provider can position and direct the electrode lead up and away from the patient's body, for example, so that the connection from the patient's shoulder to trunk cable is safe from being pulled from patient turning in bed. The notches, or wire ports, are shown in FIG. 12. The size of the notches preferably closely match the size of the wires and thus the notches are able to control the pushing and pulling of the wires from within the electrode.

Preferably, the wire connectors are adjustable (e.g. expandable to fit obese people) and durable. For example, a patient may be able roll over and the pouch will protect electrodes. Preferably, the wires can be routed around surgical sites. The wires are preferably able to be pushed back in the housing and have a controlled length removing from housing, (e.g. the wire do not fall out unintentionally). There may be 5, 3, or 2 wires organized in flat ribbon connected by insulation, or another number of wires. Preferably, the wires are comfortable against skin and present no sharp edges.

Figure 18:
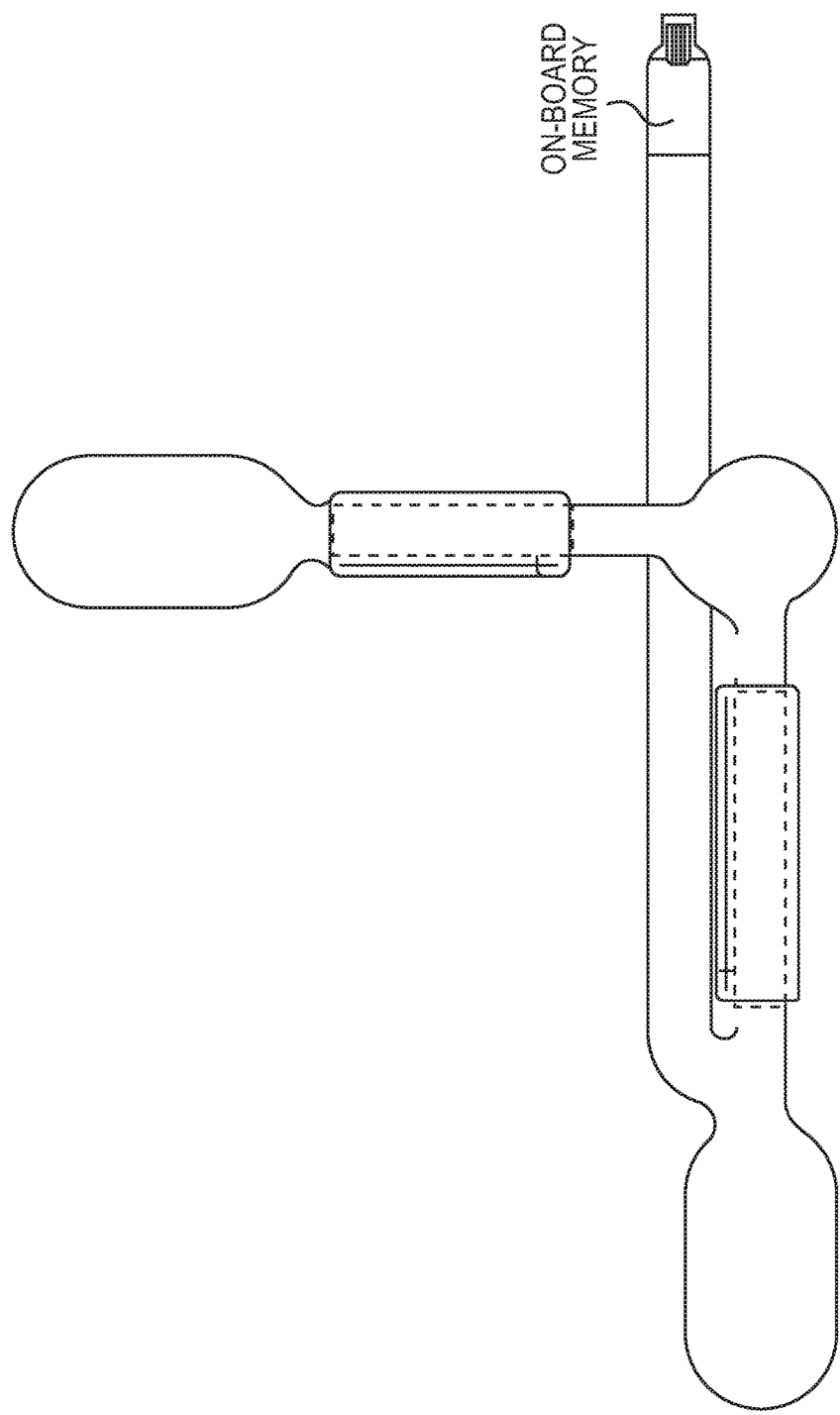
FIG. 18 depicts an embodiment of a chip installed on the backside of the padset, which is adapted to power and communicate with the chip via the connector.
Figure 19:
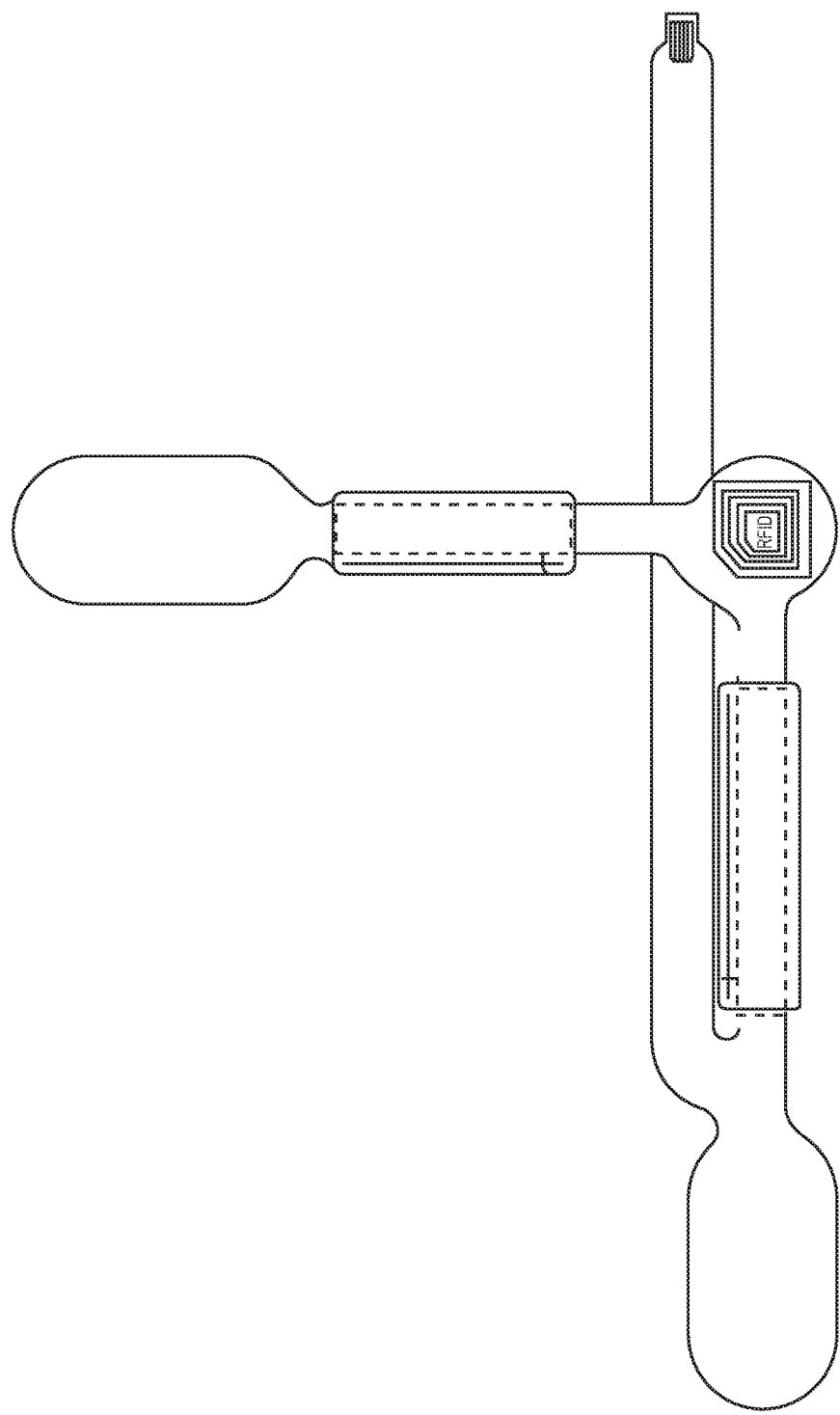
FIG. 19 depicts an embodiment of a wireless comm./memory chip (e.g. RFID) on the surface of the padset.

In another embodiment, depicted in FIGS. 18 and 19, the padset includes a memory chip containing calibration data, production data, and the like. The memory chip can be passive (e.g. RFID, SSD) or active (e.g. Bluetooth, ZigBee) and can be powered by an integrated power-cell, by the padset cable, or by a contactless inductive power source. The memory chip can be programmed with individual padset test(s) and the anticipated results from these tests. Once connected to a patient, the padset preferably communicates with the monitoring equipment and indicates what internal tests should be done and what the results should be. If there is a mismatch, a message is preferably delivered to the user. For example, in connecting a padset for normal patients to an obese patient, the padset contains information regarding the acceptable range of measured impedance and, if the readings are outside this range, the device displays an error, or, alternatively, if the padset has been outside its protective package and the exposure to air has dried out the conductive gel, the device may display an error). The internally programmed range of acceptable impedances is preferably used to identify that the memory chip can store the exact time/date when the padset was attached to a patient. After, for example, 24 hours the chip can alert the user to replace the padset.

The memory chip can store individual patient data (e.g. patient age, gender, height, weight, BMI, calibration vs. vent or spirometer) and, if unplugged from one monitoring equipment (e.g. in the OR), can immediately transfer these data to another monitor (e.g. in the PACU) assuring maximal continuity of patient care. This adaptability is useful since calibration data and equipment are not readily available to clinicians throughout the hospital.

In one embodiment the electrode pads are arranged to acquire a tetrapolar transthoracic bioimpedance signal, where some electrode pads are used to inject a stimulating current, and others are used to read the resulting voltage. In another embodiment the electrode pads are arranged to acquire multiple channels of tetrapolar transthoracic bioimpedance signals. This embodiment applies to configurations in which the separate channels share the same current-injecting electrodes, or have separate current-injecting electrodes. Further, the bioimpedance channels may be oriented at an angle between 0 and 90 degrees to each other.

In one embodiment, the electrode pads are arranged such that there is a primary bioimpedance channel and a secondary channel arranged at roughly a 45 degree angle. In this embodiment, the primary channel consists of two current-injecting electrodes and two voltage-sensing electrodes arranged such that the voltage-sensing electrodes sit close to an imaginary line connecting the two current-sensing electrodes. The secondary channel consists of two voltage-sensing electrodes. In one embodiment, the secondary channel has no current-injecting electrodes. In one embodiment, the secondary channel has exclusive current-injecting electrodes. In one embodiment, one of the voltage-sensing electrodes is shared between the primary and the secondary channels.

In one embodiment, the electrode pads are arranged to acquire a bilateral transthoracic bioimpedance signal. In this embodiment, both channels share one current-injecting electrode and one voltage-sensing electrode located just below the sternal notch. Each channel has its own current-injecting electrode and voltage-sensing electrode located on the midaxillary line on either side of the chest.

Figure 15:
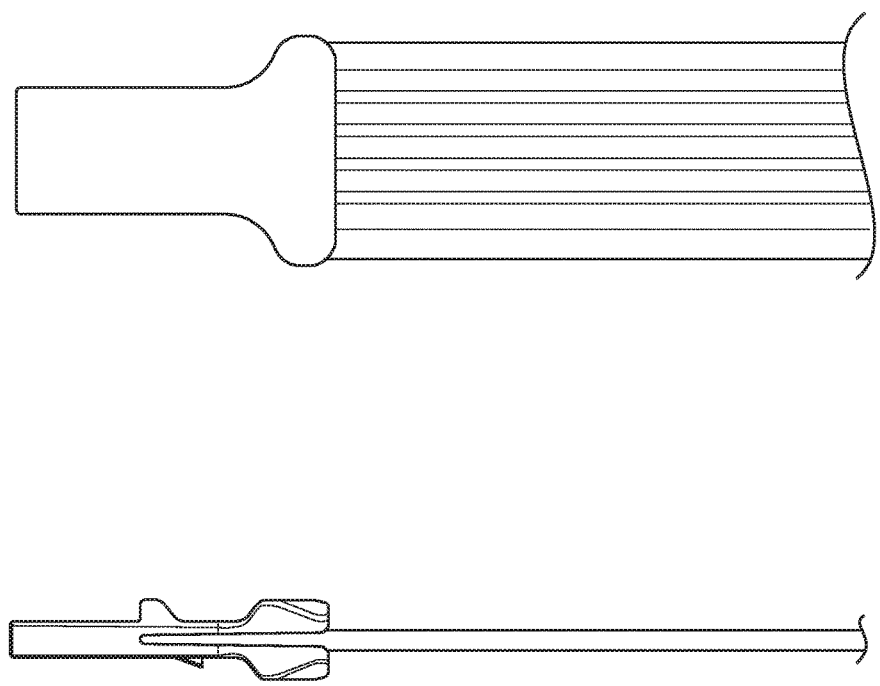
FIG. 15 depicts an embodiment of a plastic connector and traces going to electrodes.
Figure 16:
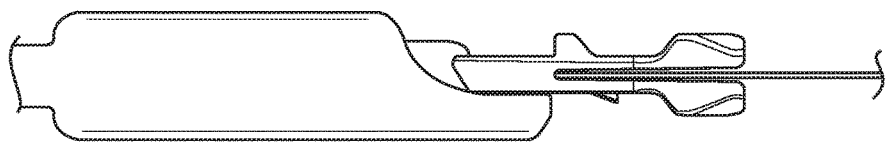
FIG. 16 depicts an embodiment of a different level of insertions of the connector and trunk cable.
Figure 16:
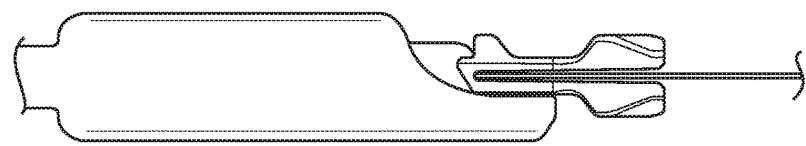
Figure 17:
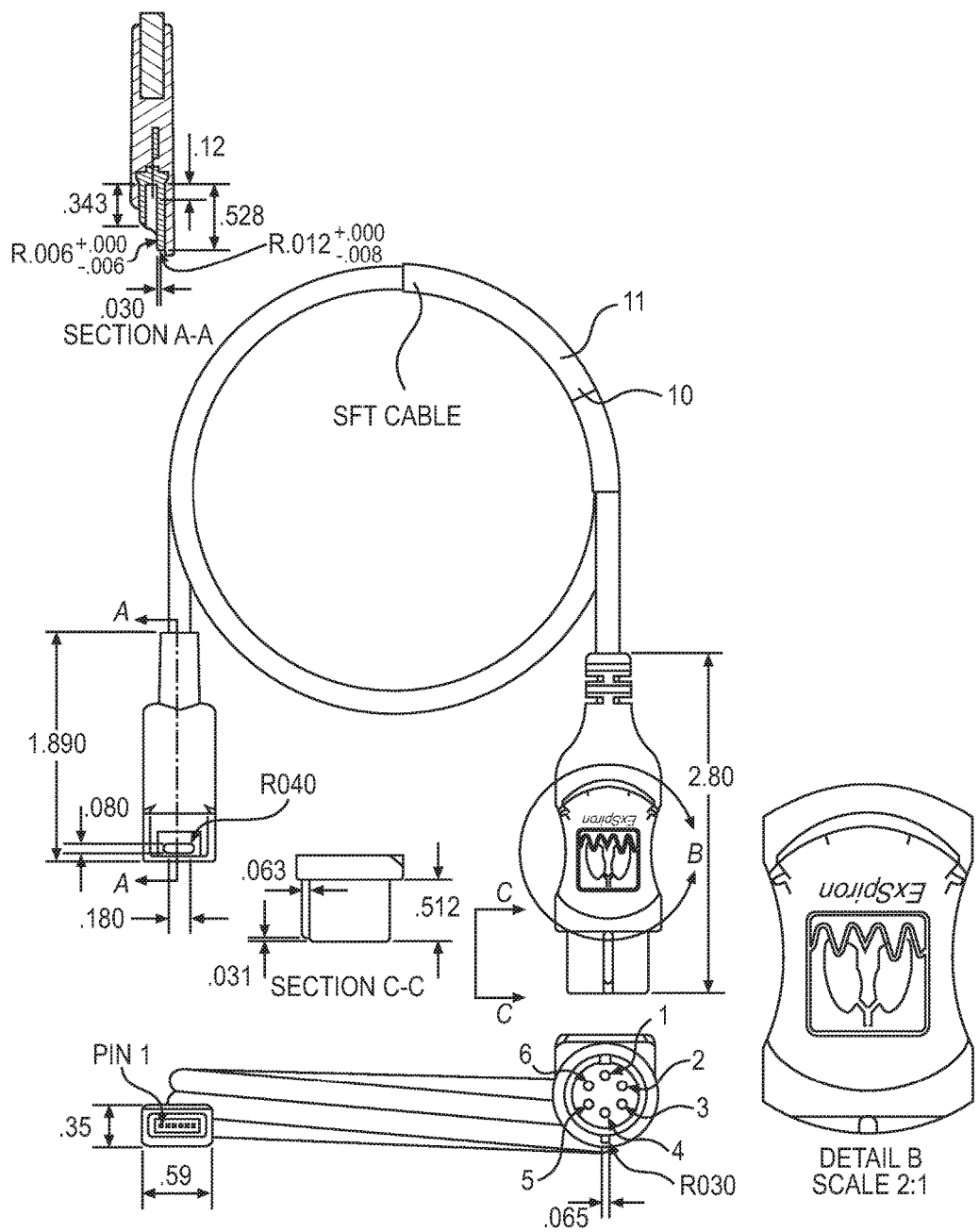
FIG. 17 depicts an embodiment of a mechanical drawing of trunk (patient) cable.

In one embodiment the attachment method of the trunk/patient cable to the connector of the electrode padset is described. The method of attachment is preferably by pinching a plastic connector housing (shown in FIGS. 13, 14 and 15) and inserting the housing (as shown in FIG. 16) into the trunk cable connection (as shown in FIG. 17). The connection is preferably a snap connection, however other connection methods can be used. The plastic connector is preferably thin, and has a feature that snaps into a recess in the reusable trunk cable. The snap feature is preferably a small ramp protruding from the connector that slides against the trunk cable connector. During the connection process the end of the ramp, which is preferably a sharp triangular feature, engages the recess of the trunk cable, creating the click and connection. When the user's fingers are removed from the connector the two flaps preferably move away from the plastic film circuit and rest against the trunk cable connector. When the user's fingers are applied to remove the connector, the ramp feature preferably moves away from the recess and the connector can be removed.

The plastic connector is preferably a housing for the end of the circuit, and provides a space for contacts to come together in a small area. The connector is preferably a simplified single entry point for the entire electrode padset system. The edges of all parts of the connector are preferably rounded so they do not etch away at the traces. The inside of the connector preferably has a feature that keeps the traces and contacts apart from each other. The connector preferably protects the circuit traces from damage during attachment or detachment. The connector preferably fans outward toward the electrodes, and provides more surface area for the pinching fingers to grip. The connector preferably has two engagement devices, one being the ramp described herein, and the other being a protrusion on the other side of the connector. The engagement devices preferably prevent the connection from being made if the connector is inserted in the wrong orientation.

The plastic connector preferably contains a slot where the film circuit and crimp contacts are inserted. The slot preferably also creates a space for the two ends of the connector to move towards when the device is pinched.

Figure 13:
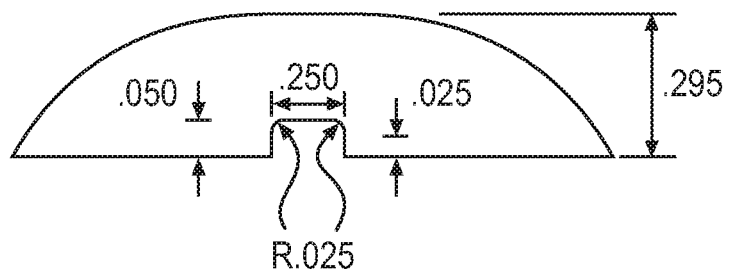
FIG. 13 depicts an embodiment of a connector.
Figure 14:
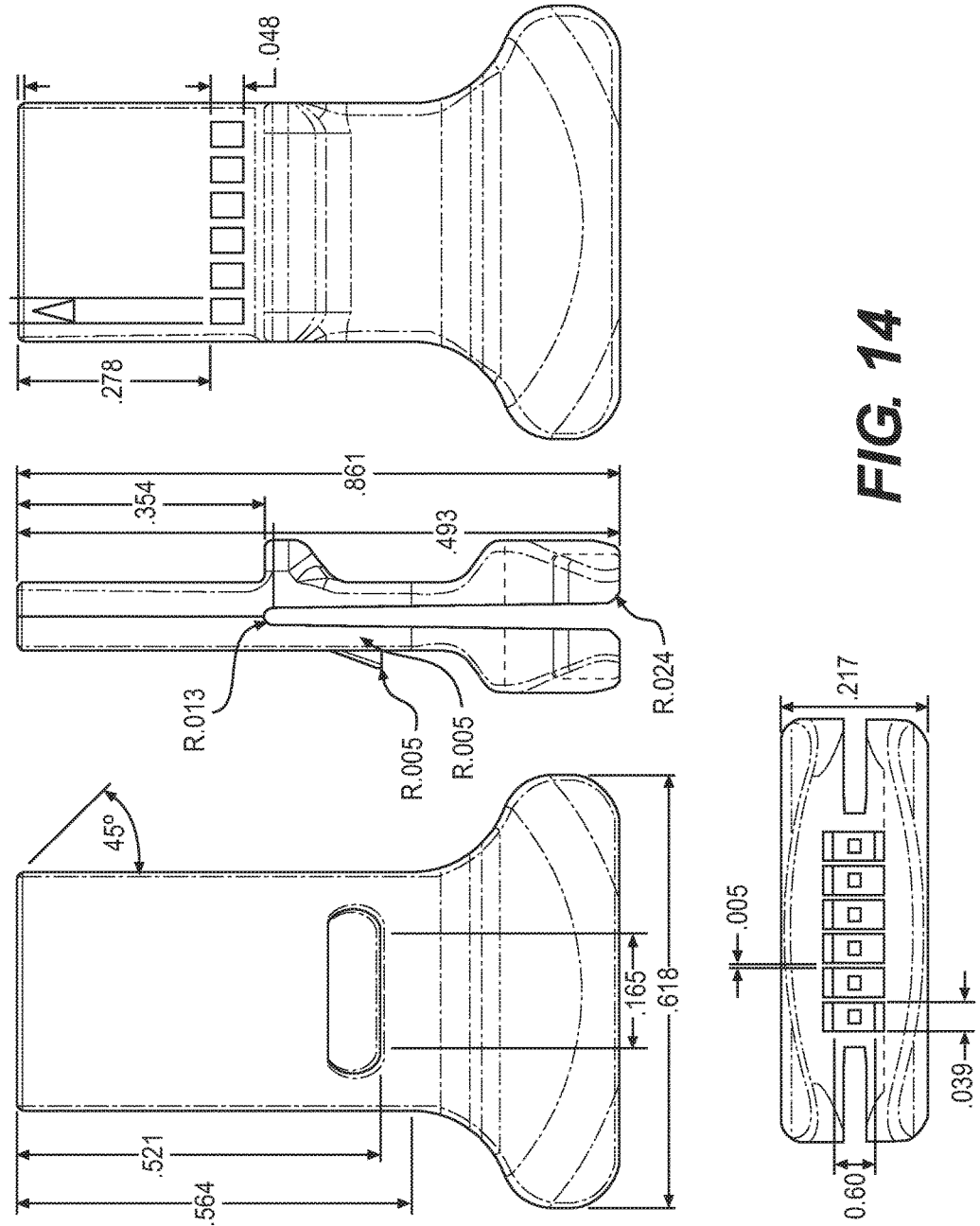
FIG. 14 depicts an embodiment of a mechanical drawing of connector.

The plastic connector preferably also provides isolation of the separate conductive elements by separating each section inside the connector (as shown in FIGS. 13 and 14). Each conductive element preferably has its own isolated compartment which provides for the necessary mechanical and electrical isolation. This isolation maintains a design which achieves a high dielectric withstand to enable the device to successfully pass a defibrillation test for medical use.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the following claims. Furthermore, the term "comprising of" includes the terms "consisting of" and "consisting essentially of."

The invention claimed is:

1. An electrode padset, comprising:
a plurality of conductive pads, at least one conductive pad adapted to emit an electrical signal and at least one other conductive pad adapted to receive an electrical signal;
electrically conductive material coupling one conductive pad to one other conductive pad and adapted to accommodate different size patients;
one pouch positioned atop each electrically conductive material and between two conductive pads, wherein a portion of excess electrically conductive material not necessary to accommodate a patient is folded and maintained within each pouch;
at least one device coupled to each pouch at least one of preventing the electrically conductive material from exiting each pouch unintentionally and allowing excess electrically conductive material to be reinserted into the pouch; and
one anti-creasing device coupled to each pouch preventing the electrically conductive material from creasing at fold points;
wherein the plurality of conductive pads are adapted to be placed on a patient in a specified configuration.

2. The electrode padset of claim 1, wherein each pouch is open at both ends.

3. The electrode padset of claim 1, wherein the electrically conductive material is adapted to fold a plurality of times within each pouch.

4. The electrode padset of claim 1, wherein the electrode padset is a single unit.

5. The electrode padset of claim 1, further comprising at least one of artwork, symbols, and indications to aid in the correct placement of the padset on a patient.

6. The electrode padset of claim 1, wherein the electrode padset is adapted to acquire at least one of electrical bioimpedance (thoracic, cardiac or otherwise), electrocardiography (ECG), electroencephalography (EEG), and electromyography (EMG) signals.

7. The electrode padset of claim 1, wherein the electrically conductive material is a vapor transmission material or a set of wires adjustable in length.

8. The electrode padset of claim 1, wherein the padset is adapted to acquire at least one channel of tetrapolar transthoracic bioimpedance signals.

9. The electrode padset of claim 8, wherein there are at least two bioimpedance channels and the bioimpedance channels are oriented at an angle between 0 and 90 degrees to each other.

10. The electrode padset of claim 1, wherein the padset is adapted to acquire a bilateral transthoracic bioimpedance signal.

11. The electrode padset of claim 1, wherein the specified configuration corresponds anatomically to a patient.

12. The electrode padset of claim 11, wherein at least one conductive pad is coupled to a patient's mid-clavicular line or sternal notch, at least one conductive pad is coupled to the patient's mid-axillary line, and at least one conductive pad is coupled to the patient's xiphoid process.

13. The electrode padset of claim 1, further comprising a memory chip.

14. The electrode padset of claim 13, wherein the memory chip stores at least one of calibration data, production data, patient data, expiration date data, and padset data.

15. The electrode padset of claim 13, wherein the memory chip is adapted to be coupled to a device capable of wireless communication.

16. The padset of claim 13, wherein memory chip is passive and is couplable to an internal or external power supply.

17. The electrode padset of claim 1, wherein the anti-creasing device is coupled inside an end of each pouch and the anti-creasing device has a curved surface for the electrically conductive material to curve a maximum of 180° around.

18. An electrode padset, comprising:
a plurality of conductive pads;
electrically conductive material coupling one conductive pad to one other conductive pad at a distance from each other;
one pouch positioned atop each electrically conductive material and between two conductive pads, wherein a portion of excess electrically conductive material not necessary to accommodate a patient is folded and maintained within each pouch;
at least one device coupled to each pouch at least one of preventing the electrically conductive material from exiting each pouch unintentionally and allowing excess electrically conductive material to be reinserted into the pouch; and one anti-creasing device coupled to each pouch preventing the electrically conductive material from creasing at fold points;

wherein the electrically conductive material is adjustable to alter the distance between the conductive pads.

19. The electrode padset of claim 18, wherein the conductive pads are adapted to receive electrical signals.

20. The electrode padset of claim 18, wherein the anti-creasing device is coupled inside an end of each pouch and the anti-creasing device has a curved surface for the electrically conductive material to curve a maximum of 180° around.

21. An electrode padset, comprising:

a plurality of conductive pads, at least one conductive pad adapted to receive an electrical signal;

electrically conductive material coupling one conductive pad to one other conductive pad;

one pouch positioned atop each electrically conductive material and between two conductive pads, wherein a portion of excess electrically conductive material not necessary to accommodate a patient is folded and maintained within each pouch;

at least one device coupled to each pouch at least one of preventing the electrically conductive material from exiting each pouch unintentionally and allowing excess electrically conductive material to be reinserted into the pouch; and at least one anti-creasing device coupled to each pouch preventing the electrically conductive material from creasing at fold points;

wherein the plurality of conductive pads are arranged in a specified configuration.

22. The electrode padset of claim 21, wherein each pouch has two open ends.

23. The electrode padset of claim 21, wherein the electrically conductive material is adapted to fold a plurality of times within each pouch.

24. The electrode padset of claim 21, wherein the electrode padset is a single unit.

25. The electrode padset of claim 21, further comprising at least one of artwork, symbols, and indications to aid in the correct placement of the padset on a patient.

26. The electrode padset of claim 21, wherein the electrode padset is adapted to acquire at least one of electrical bioimpedance (thoracic, cardiac or otherwise), electrocardiography (ECG), electroencephalography (EEG), and electromyography (EMG) signals.

27. The electrode padset of claim 21, wherein the electrically conductive material is a vapor transmission material or is a set of wires adjustable in length.

28. The electrode padset of claim 21, wherein the padset is adapted to acquire at least one channel of tetrapolar transthoracic bioimpedance signals.

29. The electrode padset of claim 28, wherein there are at least two bioimpedance channels and the bioimpedance channels are oriented at an angle between 0 and 90 degrees to each other.

30. The electrode padset of claim 28, wherein the padset is adapted to acquire a bilateral transthoracic bioimpedance signal.

31. The electrode padset of claim 21, wherein the specified configuration corresponds anatomically to a patient.

32. The electrode padset of claim 21, wherein the anti-creasing device is coupled inside an end of each pouch and the anti-creasing device has a curved surface for the electrically conductive material to curve a maximum of 180° around.

33. A method of obtaining a bioimpedance signal, comprising:

affixing the electrode padset of claim 1 to a patent;

sending an electric signal from at least one conductive pad into the patient;

receiving the electric signal from at least one conductive pad from the patient; and analyzing the received signal.

* * * * *